United States Patent
Moore

(10) Patent No.: US 7,005,935 B2
(45) Date of Patent: Feb. 28, 2006

(54) SWITCHED REACTANCE MODULATED E-CLASS OSCILLATOR

(75) Inventor: William Henry Moore, Canoga Park, CA (US)

(73) Assignee: Alfred E. Mann Institute for Biomedical Engineering at the University of Southern California, Los Angeles, CA (US)

(*) Notice: Subject to any disclaimer, the term of this patent is extended or adjusted under 35 U.S.C. 154(b) by 0 days.

(21) Appl. No.: 10/805,043

(22) Filed: Mar. 19, 2004

(65) Prior Publication Data

US 2004/0183607 A1    Sep. 23, 2004

Related U.S. Application Data

(63) Continuation-in-part of application No. 10/180,882, filed on Jun. 26, 2002, now Pat. No. 6,889,087, and a continuation-in-part of application No. 09/973,486, filed on Oct. 5, 2001, now Pat. No. 6,864,755.

(60) Provisional application No. 60/462,415, filed on Apr. 11, 2003, provisional application No. 60/456,908, filed on Mar. 21, 2003.

(51) Int. Cl.
    *H03B 11/10* (2006.01)

(52) U.S. Cl. .................. 331/166; 331/172; 331/179

(58) Field of Classification Search ............... 331/165, 331/166, 172, 177 R, 179; 327/77–79; 332/117, 332/137, 141
See application file for complete search history.

(56) References Cited

U.S. PATENT DOCUMENTS

| | | |
|---|---|---|
| 3,617,646 A | 11/1971 | Knollman |
| 3,682,160 A | 8/1972 | Murata |
| 3,995,234 A | 11/1976 | Tuccinardi |
| 4,218,772 A | 8/1980 | Sielman et al. |
| 4,245,178 A | 1/1981 | Justice |
| 4,321,706 A | 3/1982 | Craft |
| 4,539,531 A | 9/1985 | Thomas et al. |
| 4,553,110 A | 11/1985 | Kleinberg |
| 4,553,882 A | 11/1985 | Knappertz |
| 4,596,022 A | 6/1986 | Stoner |
| 4,743,789 A | 5/1988 | Puskas |
| 4,814,962 A | 3/1989 | Magalhaes et al. |
| 4,833,427 A | 5/1989 | Leuthold et al. |
| 4,916,380 A | 4/1990 | Burroughs |
| 5,053,723 A | 10/1991 | Schemmel |
| 5,193,539 A | 3/1993 | Schulman et al. |

(Continued)

OTHER PUBLICATIONS

Loeb et al. "Design and Fabrication of Hermetic Microelectronic Implants", Alfred E. Mann Institute for Biomedical Engineering, University of Southern California, (Oct. 12, 2000), presented at Microtechnology Conference, Lyons, France.

(Continued)

*Primary Examiner*—David Mis
(74) *Attorney, Agent, or Firm*—McDermott Will & Emery LLP

(57) ABSTRACT

A modulated Class E oscillator. In one embodiment, the modulated Class E oscillator may achieve high coil currents (about 1A) and voltages (about 500V) with low power components. Current may be injected when the oscillating current in the inductor passes through zero. A detector circuit may be used to trigger the current injection at the appropriate instant regardless of changes in the resonant frequency of the system. Its phase can be adjusted to compensate for propagation delays in the drive circuitry, while amplitude modulation is accomplished by switching in additional reactive conductance to increase the current injected into the tank circuit. Frequency modulation is accomplished in an alternate embodiment. The oscillator can also lock to an external reference signal and be phase modulated.

17 Claims, 8 Drawing Sheets

U.S. PATENT DOCUMENTS

| | | | |
|---|---|---|---|
| 5,193,540 | A | 3/1993 | Schulman et al. |
| 5,324,316 | A | 6/1994 | Schulman et al. |
| 5,405,367 | A | 4/1995 | Schulman et al. |
| 5,414,741 | A | 5/1995 | Johnson |
| 5,438,302 | A | 8/1995 | Goble |
| 5,486,794 | A | 1/1996 | Wu et al. |
| 5,506,547 | A | 4/1996 | Ishikawa |
| 5,543,754 | A | 8/1996 | Onodera |
| 5,643,332 | A | 7/1997 | Stein |
| 5,666,279 | A | 9/1997 | Takehara et al. |
| 5,697,076 | A | 12/1997 | Troyk et al. |
| 5,766,232 | A | 6/1998 | Grevious et al. |
| 5,798,616 | A | 8/1998 | Takehara et al. |
| 5,838,203 | A | 11/1998 | Stamoulis et al. |
| 5,872,703 | A | 2/1999 | Williams et al. |
| 6,016,257 | A | 1/2000 | Chang et al. |
| 6,046,650 | A | 4/2000 | Lichterfield |
| 6,051,017 | A | 4/2000 | Loeb et al. |
| 6,064,277 | A | 5/2000 | Gilbert |
| 6,073,050 | A | 6/2000 | Griffith |
| 6,215,365 | B1 | 4/2001 | Kurkovskiy |
| 6,225,873 | B1 | 5/2001 | Hill |
| 6,229,406 | B1 | 5/2001 | Wang |
| 6,239,665 | B1 | 5/2001 | Strom |
| 6,255,913 | B1 | 7/2001 | Wang |
| 6,268,777 | B1 | 7/2001 | Welch |
| 6,275,539 | B1 | 8/2001 | Kulha |
| 6,456,169 | B1 | 9/2002 | Oshita et al. |
| 6,462,964 | B1 | 10/2002 | Porter et al. |
| 6,469,587 | B1 | 10/2002 | Scoggins |
| 6,509,805 | B1 | 1/2003 | Ochiai |
| 6,538,521 | B1 | 3/2003 | Kobayashi et al. |
| 6,539,253 | B1 | 3/2003 | Thompson et al. |
| 6,545,554 | B1 | 4/2003 | Rozenblit et al. |
| 6,553,263 | B1 | 4/2003 | Meadows et al. |
| 6,567,703 | B1 * | 5/2003 | Thompson et al. ............ 607/60 |
| 6,593,822 | B1 | 7/2003 | Nakano et al. |
| 6,593,825 | B1 | 7/2003 | Washburn |
| 6,606,006 | B1 | 8/2003 | Alexandersson |
| 6,614,288 | B1 | 9/2003 | Dagan et al. |
| 6,621,365 | B1 | 9/2003 | Hallivuori et al. |

OTHER PUBLICATIONS

Nardin, Mark D., A Programmable Multichannel Microstimulator with Bi-Directional Telemetry, Technical Report No 254, Jan. 1996, Dept of Electrical Engineering & Computer Science, The University of Michigan, Ann Arbor. USA pp. 36-47 160-165.

Troyk et al. "Class E Driver for Transcutaneous Power and Data link for Implanted Electronic Devices" Illinois Institute of Technology, Medical & Biological Engineering & Computing, (1992), 30., pp. 69-75.

* cited by examiner

SWITCHED REACTANCE MODULATED E-CLASS OSCILLATOR

CROSS-REFERENCE TO RELATED APPLICATIONS

This application is a continuation-in-part of U.S. patent application Ser. No. 10/180,882, filed Jun. 26, 2002, now U.S. Pat. No. 6,889,087, and patent application Ser. No. 09/973,486, filed Oct. 5, 2001, now U.S. Pat. No. 6,864,755. This application is also based upon and also claims priority to U.S. provisional applications Ser. No. 60/456,908, filed Mar. 21, 2003, and Ser. No. 60/462,415, filed Apr. 11, 2003, This application is also related to U.S. Provisional Application Ser. No. 60/238,488, filed Oct. 6, 2000. The content of all of these applications are incorporated herein by reference.

BACKGROUND OF THE INVENTION

1. Field

This application relates to drive coils that generate a magnetic field to supply power and operational commands to a remote receiving coil. This application also relates generally to E-class oscillators.

2. Related Art

Many applications require or would benefit from improved efficiency in L-C tank circuit oscillations. Achieving such efficiency, however, can be problematic. One problem is now presented in the context of an exemplary application involving BIOnic Neurons (BIONs). This problem as well as other can also be present in other applications.

BIONs include micro, electrical stimulators that can be implanted within a body. BION implants may be placed in or near nerves or muscles to be electrically stimulated or at other locations. BIONs may be elongated with metallic electrodes at each end that deliver electrical current to immediately surrounding biological tissues. The implantable electronic devices may be hermetically sealed with metallic electrodes attached thereto. They may contain electronic circuitry. BION implants may be about 100 times smaller in volume than conventional implantable electronic devices such as cardiac pacemakers and cochlear implants. Their small size can result in significant physical limits on power, data transmission and packaging.

Microelectronic circuitry and inductive coils that may control the electrical current applied to the electrodes may be protected from body fluids by a hermetically sealed capsule. The capsule may be covered with a biocompatible coating or sheath for further protection. The electronic circuitry may include an inductive coil, power storage capacitor and/or integrated circuit for performing various functions.

Upon command from an external component, the implanted BION may emit an electrical stimulation pulse that travels through the body tissues between and around its electrodes. This may activate, for example, local nerve fibers. This may be part of a treatment. The BION micro stimulator may receive power and control signals from an inductive coupling to an externally generated RF magnetic field. This may be used to recharge a BION's battery and to control the timing and parameters of stimulations generation by the BION. This may be achieved by inductive coupling of magnetic fields generated by extracorporeal antenna that do not require any electrical connections to the BIONs, as discussed in U.S. Pat. Nos. 5,193,539, 5,193,540, 5,324,316, 5,405,367, and 6,051,017, incorporated herein by reference.

By selecting the appropriate strength and temporal patterning of stimulation, a desired therapeutic effect can be achieved.

The small, narrow shape of many BIONs may result in stringent requirements for wireless power, data transmission and the electromechanical assembly. Developing solutions to meet these requirements may be difficult.

For example, the inductive coupling between a primary inductive coil within an extracorporeal antenna utilized to power a BION and a small, secondary inductive coil within the BION itself may be difficult to establish and maintain within the stringent requirements of the BION's power, data transmission, and electromechanical assembly. One reason for this may be that the coefficient of inductive coupling between a large primary coil and a distant, small secondary coil across an air gap may be very low, e.g., less than 2%. Therefore, the BION may be assembled such that the length and the cross-sectional area of its receiving coil are maximized. However, the BION's small size may limit the BION's receiving coil size.

To compensate for a weak coupling coefficient, the strength of the primary RF magnetic field, generated by the extracorporeal antenna, for example, may be made high. However, excessive power dissipation may be undesirable. For example, the extracorporeal antenna may be driven to at least 200–400V or even at 500V in order to generate sufficient power to drive the remote, implanted BION. However, designing an appropriate oscillator to generate sufficient field strength can be problematic.

As is well understood in the art, power oscillators are often classified according to the relationship between the output voltage swing and the input voltage swing. It is often the design of the output stage that defines each class. Classification may be based on the amount of time the output devices operate during one complete cycle of signal swing. This may also be defined in terms of output bias current, or the amount of current flowing in the output with no applied signal.

Conventional A-Class amplifiers may not be efficient enough for field use, as they can exhibit significant power dissipation. An alternative choice is an E-Class amplifier, or E-Class oscillator. Class E operation may involve oscillators designed for rectangular input pulses, not sinusoidal waveforms. The output load may be a tuned circuit, with the output voltage resembling a damped single pulse. A Class-E oscillator may operate in a switched mode (ON or OFF) which can provide a very high collector efficiency that can theoretically approach 100%. In operation, the energy content, or drive level, of an inter-stage signal may be applied to a single RF transistor. In combination with a temperature-compensated bias circuit, the single transistor may be set so that the single RF transistor is always sufficiently driven ON or OFF with each cycle of the inter-stage signal, but is not overdriven ON or OFF.

The high field strength and low power dissipation requirements of some BION applications might be accomplished by using Class E amplification with a very high Q (>100) tuned circuit. However, it may be unclear how to effectively utilize a Class E oscillator in a BION application, where both power efficiency and data transmission are often needed.

These requirements can be in conflict, as power efficiency often requires highly resonant operation of the Class E oscillator, while data transmission often requires rapid modulation of the Class E oscillator. With respect to the rapid modulation, a problematic feature of the Class E oscillator, in BION applications, can be that both the position and duration of the drive pulse are critical. For a coil frequency of 2 MHz, any drive pulse over 125 ns can cause excessive power dissipation in the switch without significantly increasing the energy in the coil. However, producing various pulse widths can require additional components that increase the cost and size of the coil driver assembly, which can be impractical in BION applications.

Using a Class E oscillator in BION applications can cause additional problems. For example, the flexible shape of the BION may easily be deformed while it is worn by the patient. Such deformities can cause fluctuations in the inductance of the external coil, and a Class E oscillator may not inherently compensate for such fluctuations. Moreover, the electromechanical assembly requirements of BIONs can make it desirable to accommodate the driver circuitry on the coil itself. This type of construction can make a typical Class E oscillator unsuitable for BION applications. Further, complicated circuitry can be required to change pulse width for achieving desired AM modulation, when utilizing a typical Class E oscillator. Changes in pulse width can be undesirable because they can cause significant degradation of efficiency, something a battery-operated BION may have limited capacity to endure.

BIONs are an exemplary application. A number of other applications, such as radio communication, metal detectors, mine detection, or power and data transmission to many types of remote devices, may also benefit from an oscillator having an efficient driving mechanism.

BRIEF SUMMARY OF INVENTION

An E-Class oscillator may be configured to lock to an external reference signal. The oscillator may include a tank circuit configured to oscillate; a first switching circuit configured to repeatedly add energy into the tank circuit in response to a drive signal to maintain the oscillation of the tank circuit; a second switching circuit configured to controllably alter the oscillation frequency of the tank circuit; and a controller configured to generate a control signal based on the external reference signal and based on the drive signal that causes the second switching circuit to repeatedly alter the oscillation frequency of the tank circuit in a manner that causes the oscillator to lock to the external reference signal.

The controller may include a D memory. The D memory may have a clear input and the clear input may be configured to be in communication with the external reference signal. The D memory may have a clock input and the clock input may be configured to be in communication with the drive signal.

The E-Class oscillator may include a feedback circuit in communication with the tank circuit that is configured to generate the drive signal. The feedback circuit may include a zero crossing detector and a pulse generator circuit. The feedback circuit may include a phase shifter circuit.

The controller may be configured to repeatedly alter the oscillation frequency by repeatedly increasing the frequency in response to either the external reference signal or to the drive signal and by repeatedly decreasing the frequency in response to the other of these signals.

The E-Class oscillator may include a reactance that is configured to be added to and removed from the tank circuit by the second switching circuit.

The controller may be configured to repeatedly add the reactance to the tank circuit in response to either the external reference signal or to the drive signal and to repeatedly remove the reactance from the tank circuit in response to the other of these signals.

A process for locking an E class oscillator having a tank circuit to an external reference signal may include repeatedly adding energy into the tank circuit in response to a drive signal; and repeatedly altering the oscillation frequency of the tank circuit in response to the drive signal and the external reference signal in a manner that causes the oscillator to lock to the external reference signal.

The oscillator may include a reactance and the repeatedly altering the oscillation frequency may include repeatedly adding the reactance to the tank circuit in response to either the external reference signal or to the drive signal; and repeatedly removing the reactance from the tank circuit in response to the other of these signals.

The frequency of the external reference signal may be modulated and the frequency of the E-Class oscillator may track the modulation.

The phase of the external reference signal may be modulated and the phase of the E-Class oscillator may track the modulation.

A process for modulating the phase of an E-Class oscillator in accordance with the modulated phase of an external reference signal may include repeatedly altering the frequency of the oscillator in response to the external reference signal in a manner that causes the phase of the oscillator to substantially track changes in the phase of the external reference signal.

The E-Class oscillator may include a tank circuit and the repeatedly altering the oscillation frequency may include repeatedly adding the reactance to and removing it from the tank circuit.

These, as well as other objects, features and benefits will now become clear from a review of the following detailed description of illustrative embodiments and the accompanying drawings.

DETAILED DESCRIPTION OF ILLUSTRATIVE EMBODIMENTS

In the following description of illustrative embodiments, reference is made to the accompanying drawings. It is to be understood that other embodiments may be utilized and structural and functional changes may be made without departing from the scope of the concepts that are presented.

Figure 1:
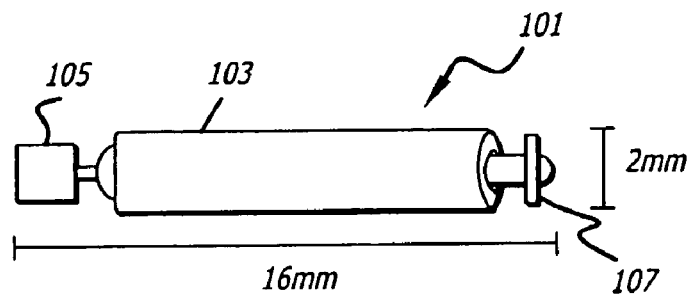
FIG. 1 illustrates an exemplary design and fabrication of a BION micro stimulator.

FIG. 1 illustrates a BION 101. It may be encased in a glass sheath 103 and may have two electrodes, a Ta electrode 105 and an Ir electrode 107. BION 101 may have a size of about 2 mm in diameter and 16 mm in length. The small size may allow the BION to be implanted by injection in an outpatient procedure that may be performed by a physician. The size may allow the BION to be placed in a small, deep, or hard-to-reach muscle that may be difficult to stimulate effectively from the skin surface. The small size and wireless nature of the implantable BION may minimize the threat of infection, skin breakdown, and tissue damage. Other types of implants may be too large, particularly in areas where multiple implants are required, or have many long leads.

Figure 2:
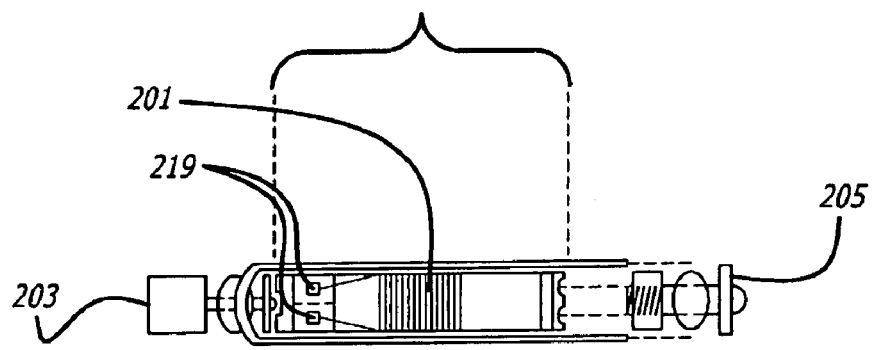
FIG. 2 illustrates a capsule subassembly of the BION illustrated in FIG. 1.
Figure 3:
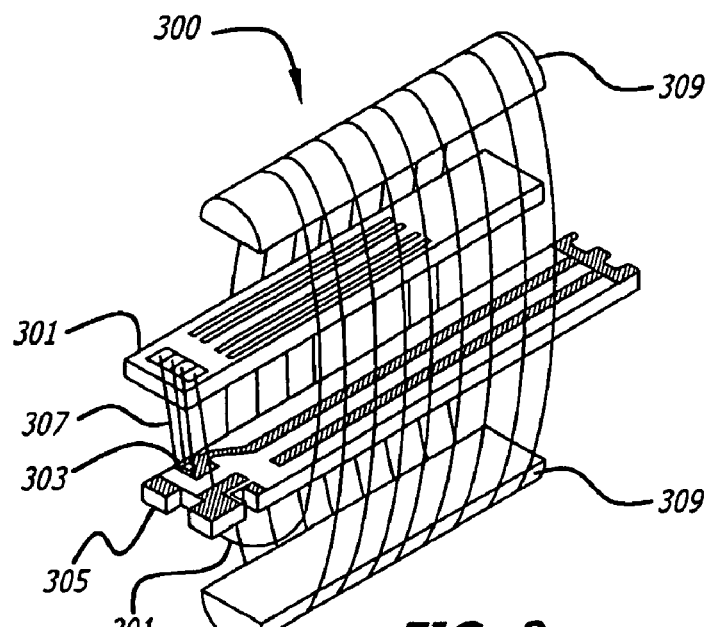
FIG. 3 illustrates an exploded view of an electronic subassembly of the BION illustrated in FIG. 1.

FIGS. 2 and 3 illustrate electronic circuitry in an exemplary BION. As shown in FIG. 2, a self-resonant receiving coil 201 may be located between two electrodes: a capacitor electrode 203 and a counter electrode 205. FIG. 3 shows that receiving coil 201 may be wound about an integrated circuit chip (IC) 301, a diode chip 303 such as, for example, a Schottky diode, and two semi-hylindrical ferrites 309. IC 301 may derive DC power by rectifying and filtering carrier energy picked up by the receiving coil 201. The carrier may provide a synchronous clock and its modulations encode a serial bit stream, which may be decoded by a state machine in IC 301. The first data byte may specify an address, which is compared to an address specified by a hardwired read-only memory in IC 301. If the addresses match, subsequent data bytes may be decoded to specify the desired operation of the BION. In an exemplary embodiment, stimulation operations may require a pulse width and a pulse amplitude specification, which may be contained within the encoded serial bit stream received by receiving coil 201 and encoded by IC 301.

Stimulation to activate a muscle may comprise relatively brief pulses, such as 0.2 ms, at low frequencies, such as less than 20 pps. During the inter-pulse period, which may be greater than 50 ms, energy may be stored in an electrolytic capacitor. Continuing with FIG. 2, the electrolytic capacitor may comprise a combination of the capacitor electrode 203 and body fluids. Counter electrode 205 may resist polarization under all sequences of charging and discharging of the capacitor electrode 203. When the carrier is on, but the implant is idle, capacitor electrode 203 may be charged until it becomes fully polarized. In the exemplary embodiment described herein, this charging may be accomplished at one of four selectable rates, such as at 0, 10, 100 and 500 micro amps. Full polarization may be achieved at approximately +17 volts DC.

Sensing functions may also be provided and may use a back-telemetry link that operates during pauses in the external carrier, during which an external coil, worn by the patient, may act as a receiving antenna. Self-resonant coil 201 in the BION may act as part of the tank circuit for an oscillator that is modulated to transmit digitized data obtained from a previously commanded sensing operation. Three sensing modalities may be used. A Bioelectrical recording sensing modality may utilize voltages present on electrodes 203 and 205 that can be amplified, integrated and digitized according to gain and timing programmed by the command that initiates the sensing operation. Such data may represent the impedance of the tissue through which a current pulse is being delivered simultaneously, the electrical field created in the tissue by a stimulus pulse from another implant, or a bioelectrical signal such as electromyographical activity. An acceleration sensing modality may incorporate micro-electromechanical silicon systems (MEMS) into the BION to sense acceleration or inclination with respect to the gravitational field of the BION implant. A relative position sensing modality may utilize the dependence of a detected signal on the distance and relative orientation between emitting and detecting BIONS. Changes in a patient's limb posture may produce relative motion of BIONS located in the patient's various muscles, permitting limb posture and motion to be inferred from a set of coupling strengths among several implanted BIONS.

Proceeding with FIG. 3, electronic subassembly 300 may include a ceramic two-sided micro-printed circuit board (PCB) 305, which may provide a mechanical platform for the inside of electronic subassembly 300 and may make all of the electrical interconnections on both surfaces and ends. On one side, .PCB 305 may carry IC 301, diode chip 303, and conventional gold wirebonds 307 to the substrate of PCB 305 which may be, for example, alumina. The hemicylindrical ferrites 309 may be glued to the top and bottom surfaces of subassembly 300, and self-resonant coil 201 may be wound over the ferrites 309 and solder-terminated to the back of PCB 305. Although not illustrated in FIG. 2 and FIG. 3, self-resonant coil 201 may have approximately 200 windings. Solder terminations 219 are visible in FIG. 2.

BION 101 may receive commands and send signals through RF power and communications supported by an E-Class oscillator design. BION 101 may draw very little power using an inductive coupling between its receiving coil 201 and a wearable, primary coil worn by a patient. The two coils may have a very low coupling coefficient, such as less than 3%, due to their physical separation and mismatch in size. Such a low coupling coefficient may require an intense RF magnetic field for power and communications, such as 1A at 500V peak in the wearable, primary coil. The coil may have about 4–6 turns of 18 gauge stranded wire.

To generate a strong magnetic field efficiently, the oscillator may utilize a very high Q tank circuit. This may consist of a wearable, primary coil and a small tuning capacitor. The Q may be around 100. By switching in different capacitors, the reactance of the primary coil may be changed to effectuate modulation, such as amplitude modulation, without requiring complicated circuitry. Changes in pulse width may be undesirable because they may cause significant degradation of efficiency.

The oscillator may inject a brief current pulse into the tank circuit only at a time when the current through the wearable, primary coil is passing through zero and the voltage across the driving Metal-Oxide-Semiconductor Field-Effect-Transistor (MOSFET) of the E-Class oscillator is at its negative peak.

The oscillator circuit may further include a feedback circuit, including an adjustable phase shift and zero-crossing detector which may compensate for propagation delays in the drive circuitry, as well as shifts in resonant frequency that may result from deformation of the coil, such as when the patient moves. All reactive components may be selected to minimize dissipation and may include, for example, silver mica capacitors, highly stranded antenna wire, and very fast transistors.

Figure 4:
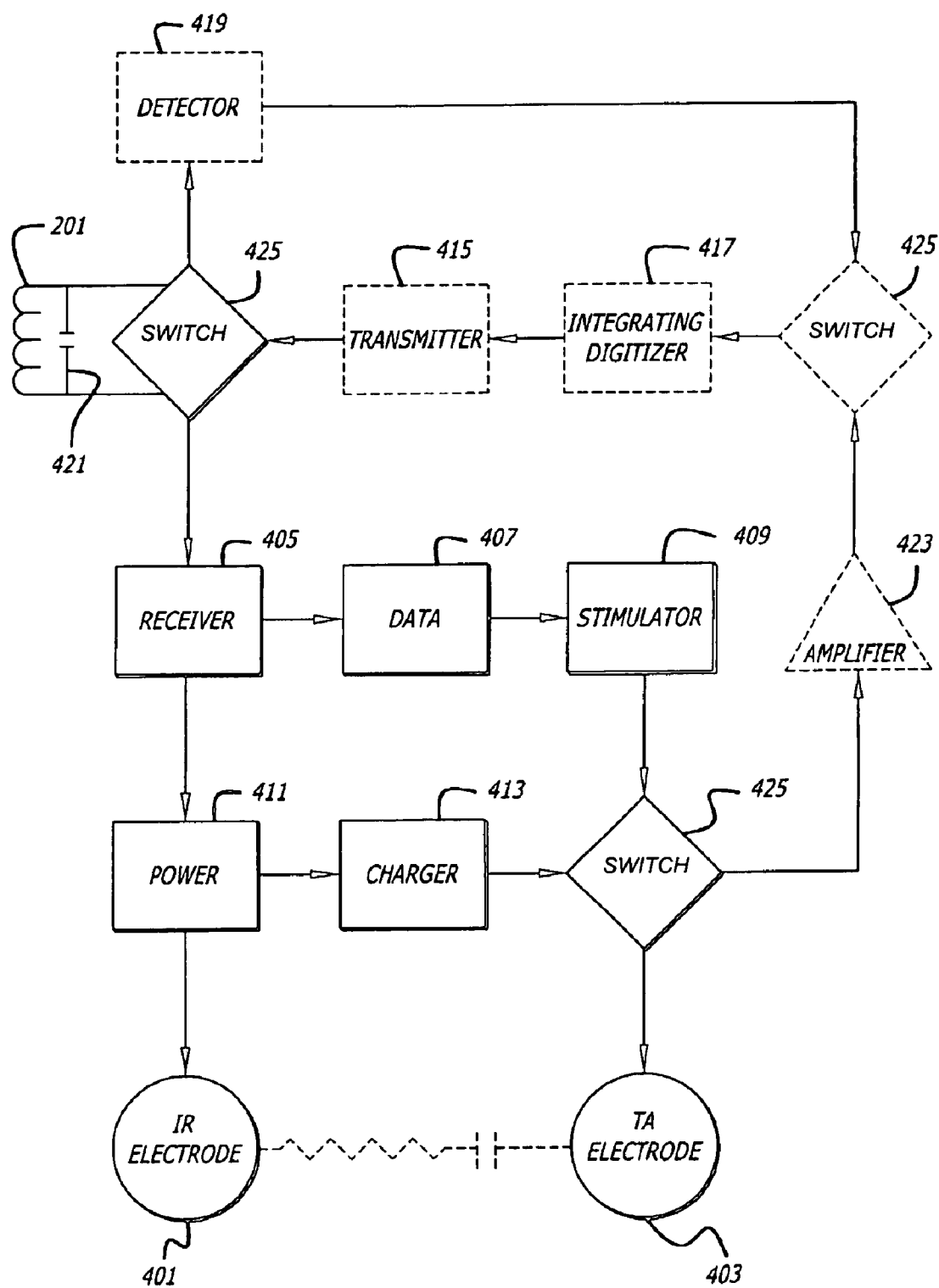
FIG. 4 illustrates internal, implantable components of an exemplary BION system architecture.
Figure 5:
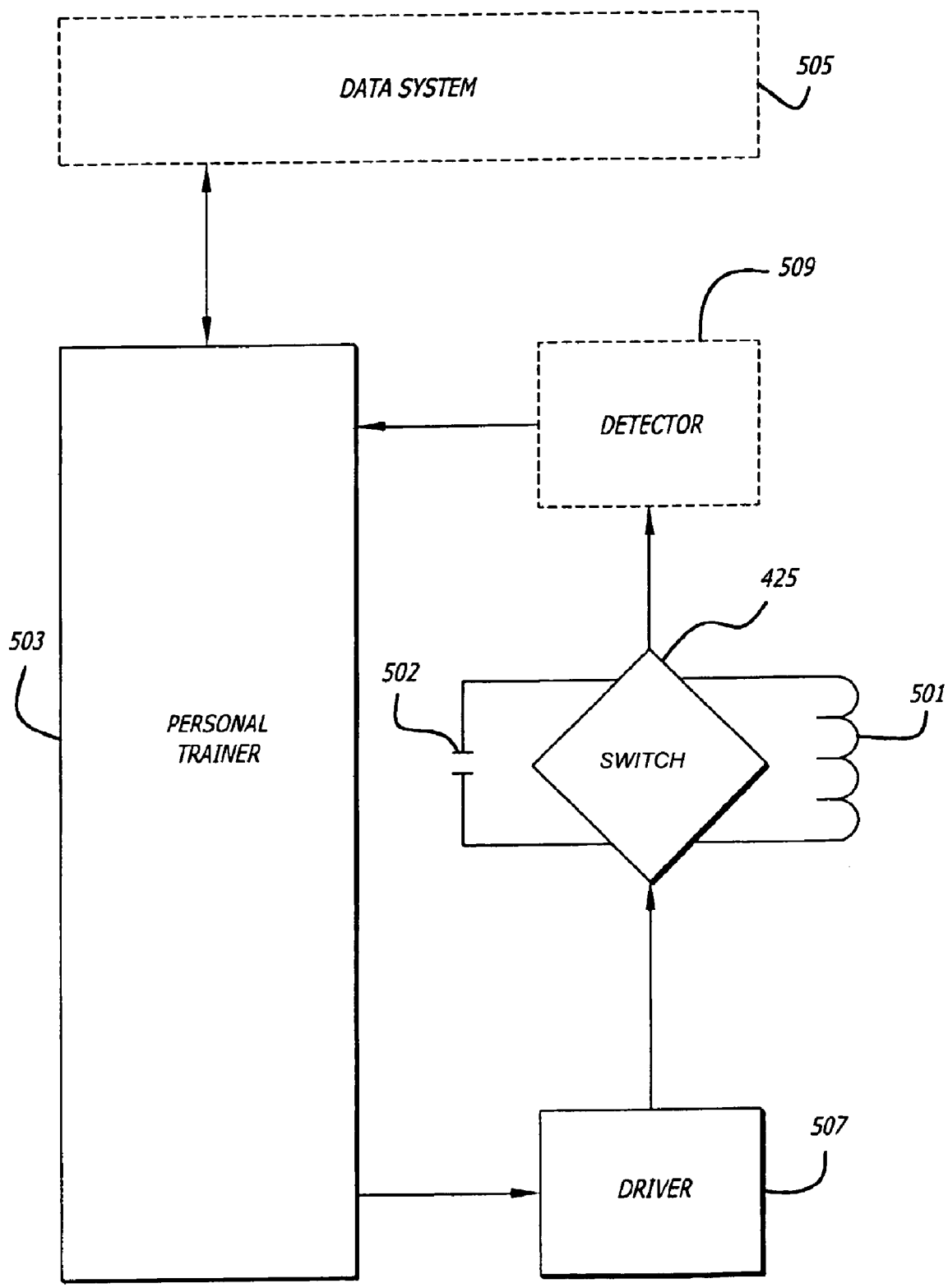
FIG. 5 illustrates external components of the exemplary BION system architecture of FIG. 2.

FIG. 4 and FIG. 5, together, illustrate an exemplary BION system architecture. FIG. 4 and FIG. 5 are directed to the internal circuitry of an implantable BION and to the external circuitry involving the wearable, primary coil, respectively. Power and communication transmissions may occur between the internal and external circuitry through a patient's skin and, specifically, may be achieved by inductive coupling between a self-resonant coil 201 in FIG. 4 and a magnetic field generated by a wearable, primary coil 501 in FIG. 5.

FIG. 4 illustrates functions of electronic subassembly 301. Capacitor electrode 401 and counter electrode 403 may transmit signals from electronic subassembly 301. Electronic subassembly 301 may receive data, as illustrated by a block 405, decode data as illustrated by a block 407, and create a stimulating charge, as illustrated by a block 409. Additionally, electronic subassembly 301 may provide power as illustrated by a block 411 and generate charge as illustrated by a block 413. A feedback circuit may include an integrating digitizer, as illustrated by a block 415, a transmitter as illustrated by a block 417, and an adjustable phase shift and zero-crossing detector as illustrated by a block 419. A tuning capacitor 421 may also be included in the feedback circuit. Once a stimulating charge has been determined as illustrated by a block 409, it may be amplified as illustrated by a block 423. Blocks 425 may represent switching functions.

FIG. 5 illustrates external components of BION systems that can be utilized with an efficient modulated Class E oscillator. The wearable, primary coil described above may include the transmission coil 501. The resonant frequency of the tank circuit of the oscillator may be set by the transmission coil 501 and a capacitor 502. Transmission coil 501 may be sized and shaped for the body part to be stimulated, and may have an integral small enclosure for its tuned RF power circuitry that connects to and is controlled by a personal trainer 503. The personal trainer 503 may function like a very large, externally synchronized shift register to produce previously stored sequences of carrier modulations that activate the patient's various BION implants. In an exemplary embodiment, the personal trainer 503 may comprise a 68HC11 microcontroller with battery-backed RAM, powered by a conventional AC-DC converter that plugs into an AC power outlet. A clinician may use a personal computer to load exercise programs into the personal trainer 503, which may convert those programs into sequences of modulation of the 2 MHz carrier. Transmission coil 501 may generate the 2 MHz magnetic field that powers and commands the BION functions with commands as described above.

An internal microcontroller within personal trainer 503 may monitor, timestamp and record all usage of its programs by a patient. These data may then be uploaded to a data system 505 when a patient has completed a personal trainer program, and the data system may adjust stimulation parameters for follow-up treatment.

Figure 6:
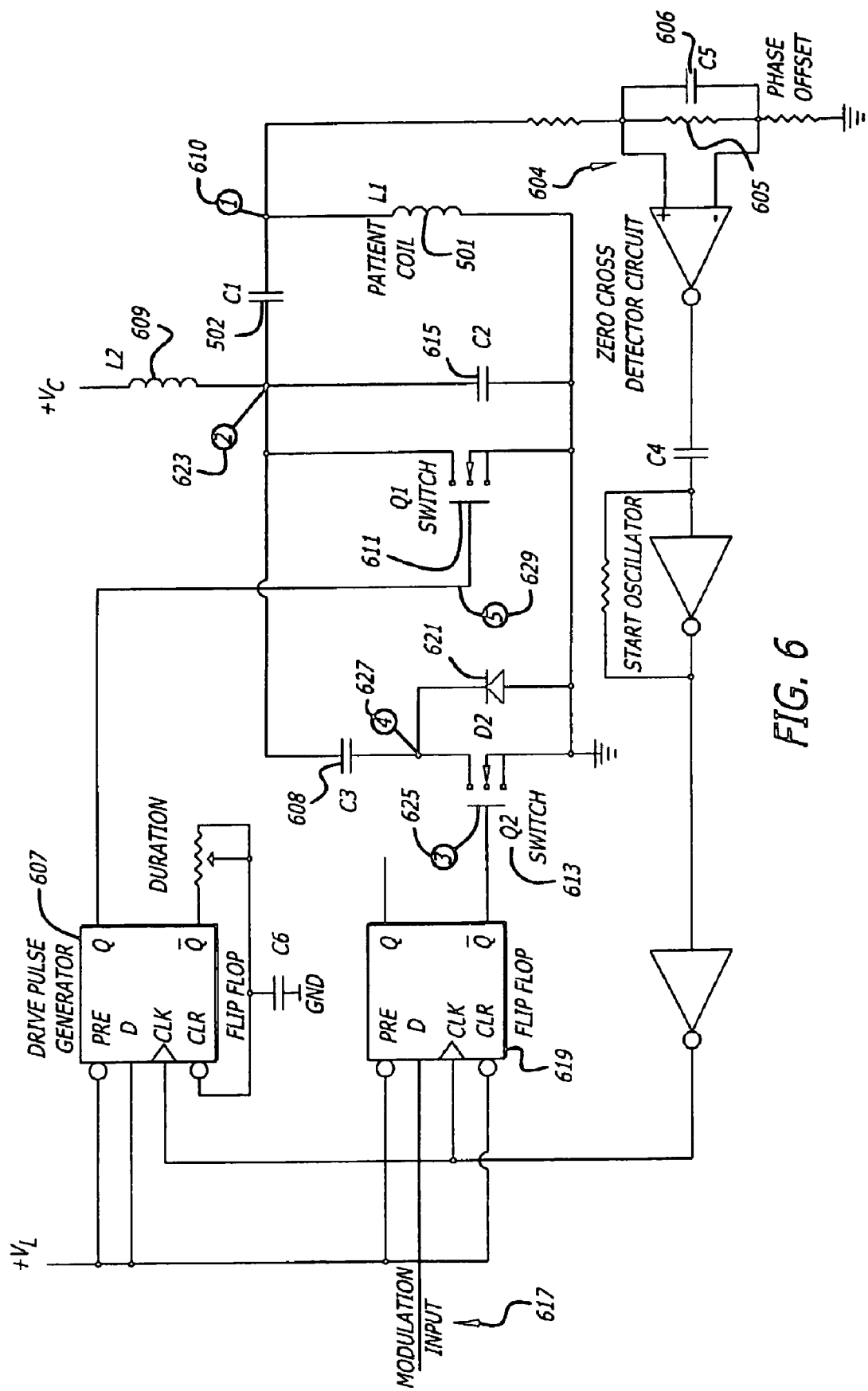
FIG. 6 illustrates an exemplary Class E modulated power oscillator circuit utilized in one embodiment for amplitude modulation.
Figure 7:
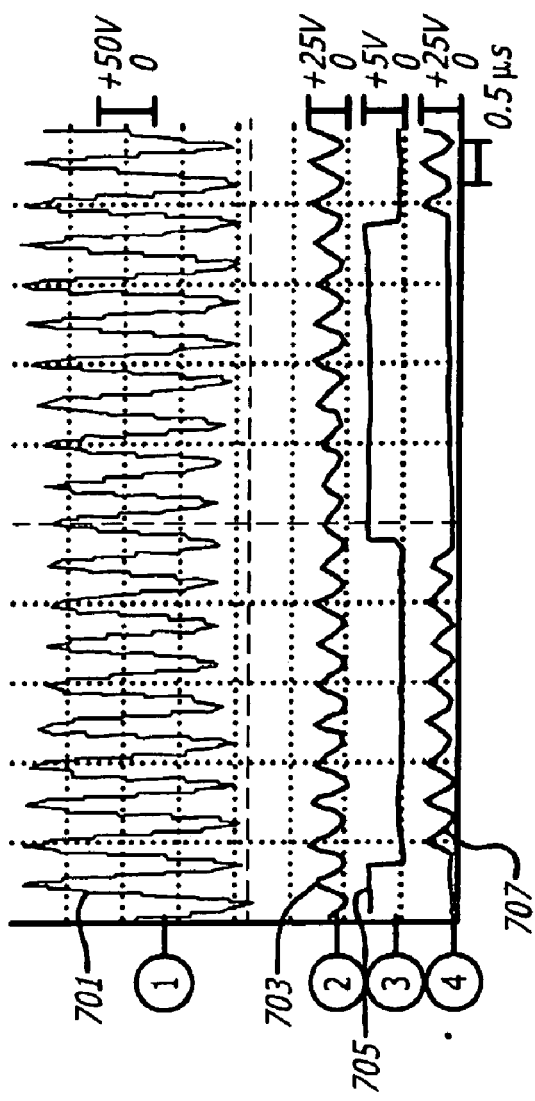
FIG. 7 illustrates exemplary waveforms at various test points in the circuit illustrated in FIG. 6.
Figure 7:
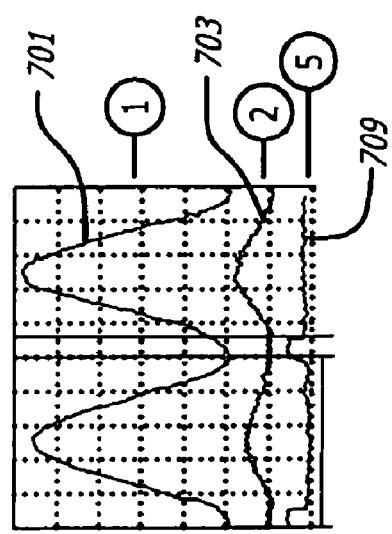

FIG. 6 illustrates an exemplary schematic for an oscillator design. The design may include circuitry for modifying a Class E oscillator with switched reactance modulation. As will be apparent to those skilled in the art, the resonant frequency of the tank circuit may be set by the transmission coil 501 (worn by the patient) and the capacitor 502, which were discussed above in connection with FIG. 5. The zero-crossing of the current in the inductor may be signaled by a zero cross detector circuit 604. A resistor 605 and capacitor 606 may cooperate to shift the phase of the voltage across the inductor L1 by approximately 90 degrees, thus causing the zero crossing of the current in the inductor 501 to substantially coincide with the zero crossing of the voltage across the resistor 605 or capacitor 606. This zero crossing signal may be used to fire pulse generator 607 for a preset duration that straddles the time when the current in inductor 501 is zero. This is the point when power injection is most efficient. Modulation may be accomplished by switching in parallel capacitor 608, which may increase the current drawn into the tank circuit through choke 609, in turn increasing the amplitude of the oscillations to a new steady state over about four carrier cycles. These oscillations may be measured at test point 1, indicated at location 610 by a test point indicator marked as an encircled numeral. This test point indicator, as well as four others (marking test points 1 through 5) may correspond to the waveforms shown in FIG. 7. Specifically, signal 701 in FIG. 7 may correspond to test point 1, indicated at 610 in FIG. 6; signal 703 in FIG. 7 may correspond to test point 2, indicated at 623 in FIG. 6; signal 705 in FIG. 7 may correspond to test point 3, indicated at 625 in FIG. 6; signal 707 in FIG. 7 may correspond to test point 4, indicated at 627 in FIG. 6; and, signal 709 in FIG. 7 may correspond to test point 5, indicated at 629 in FIG. 6. As will be appreciated by those skilled in the art, these waveforms are exemplary of the functioning of the oscillator circuit.

Further describing the switched reactance modulated oscillator circuit, the exemplary circuit illustrated in FIG. 6 may use a technique that requires only one pulse width of ideal duration. Switched reactance modulation may be used to encode data on the carrier. Specifically, as it applies to the present invention, switch 611 may provide a fixed drive pulse width. When switch 613 is open, capacitor 608 may not be in the series resonant path and the sine wave voltage at the junction of transmission coil 501 and capacitor 503 may be at some present minimum defined by the losses in the tank circuit versus the regenerative current pulses, whose amplitude depends on the value of capacitor 615. When switch 613 is closed, on the other hand, capacitor 608 may be in the series resonant path, providing additional capacitance in parallel with capacitor 615 and increasing the injected current, which in turn may increase the amplitude of the oscillations in the tank circuit.

Modulation input 617 may be applied through flip flop 619 to synchronize changes in the state of MOSFET switch 613 (test point trace 3) with the zero current points detected by feedback circuit 604. Diode 621 may provide the current charge path from ground to capacitor 608 (test point 4). The current discharge path may be provided by MOSFET 613. When MOSFET 613 is turned off, capacitor 608 may be, in effect, removed from the circuit. As will be appreciated by those skilled in the art, by using various values for the ratio of capacitor 615 to capacitor 608, the same circuitry can be used to generate primarily frequency modulation rather than amplitude modulation.

Figure 8:
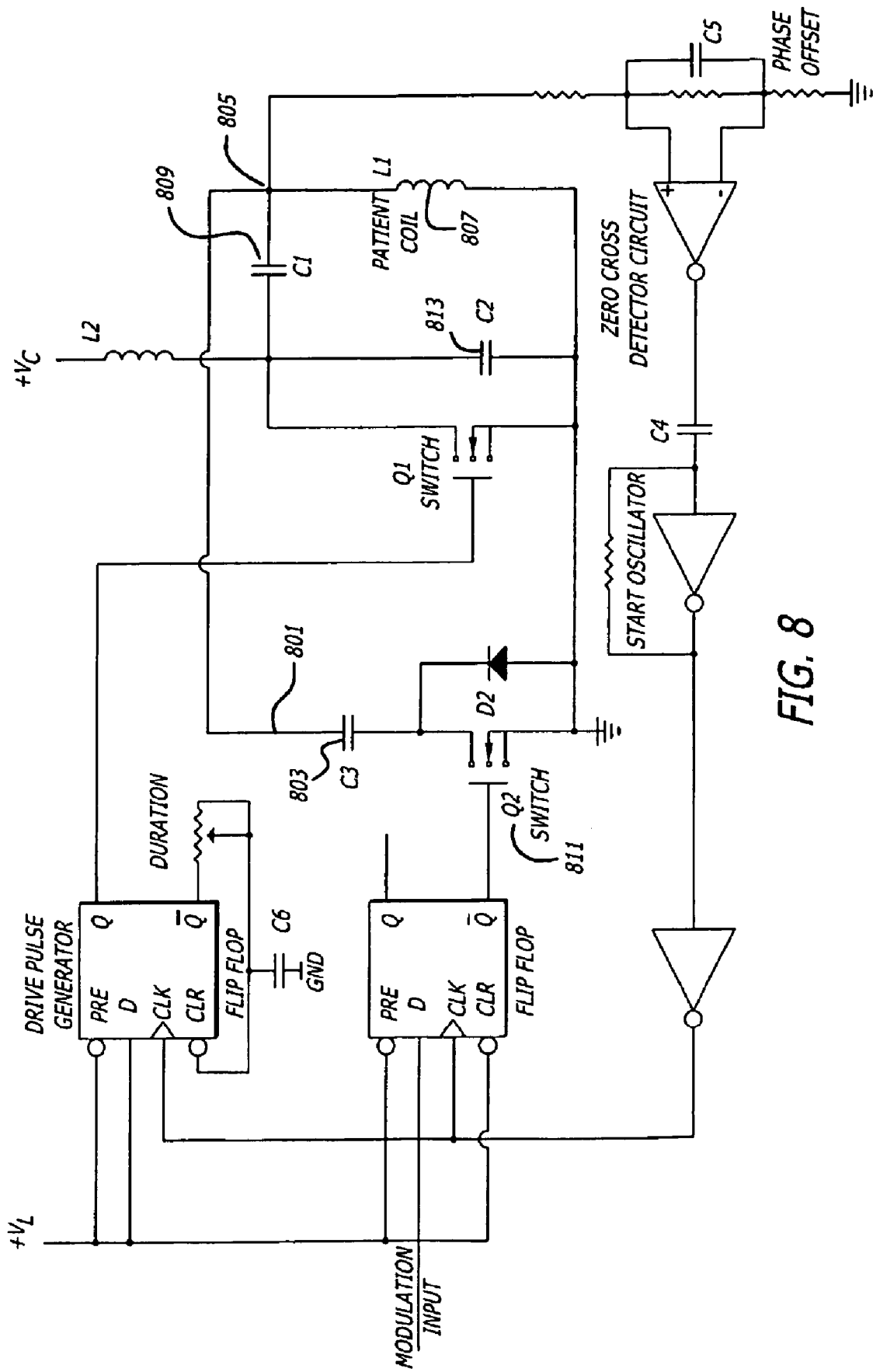
FIG. 8 illustrates an exemplary Class E modulated power oscillator circuit utilized in another embodiment that provides frequency modulation.

FIG. 8 illustrates an exemplary Class E modulated power oscillator circuit utilized in another embodiment that advantageously provides frequency modulation. This embodiment is identical to the one shown in FIG. 6 and operates in the same way, with one notable exception. One of the connections 801 to capacitor 803 is connected to the junction 805 between the patient coil 807 and tank capacitor 813. When connected in the circuit by switch 811, the capacitor 803 is effectively placed in parallel with the patient coil 807. With appropriate values for the capacitors, this alternate embodiment causes the oscillations to be frequently modulated by the modulation input, rather than amplitude modulated. Although frequency modulation can also be effectuated through the selection of appropriate values of the capacitors in the circuit shown in FIG. 6, the configuration shown in FIG. 8 may provide superior results.

It is, of course, to be understood that numerous values could be chosen for the capacitors and coil in the circuits shown in FIGS. 6 and 8. The following values are known to work: capacitors 608 and 803: 680 pf; capacitors 615 and 813: 2700 pf; capacitors 502 and 809: 680 pf; and coils 501 and 807: 10 uh.

The embodiment of the E-Class oscillator shown in FIG. 8 may be phase modulated. In this embodiment, the phase of the input signal may be modulated. The output of the E-Class oscillator may substantially track this phase modulation. The circuit shown may intrinsically accomplish this.

Figure 9:
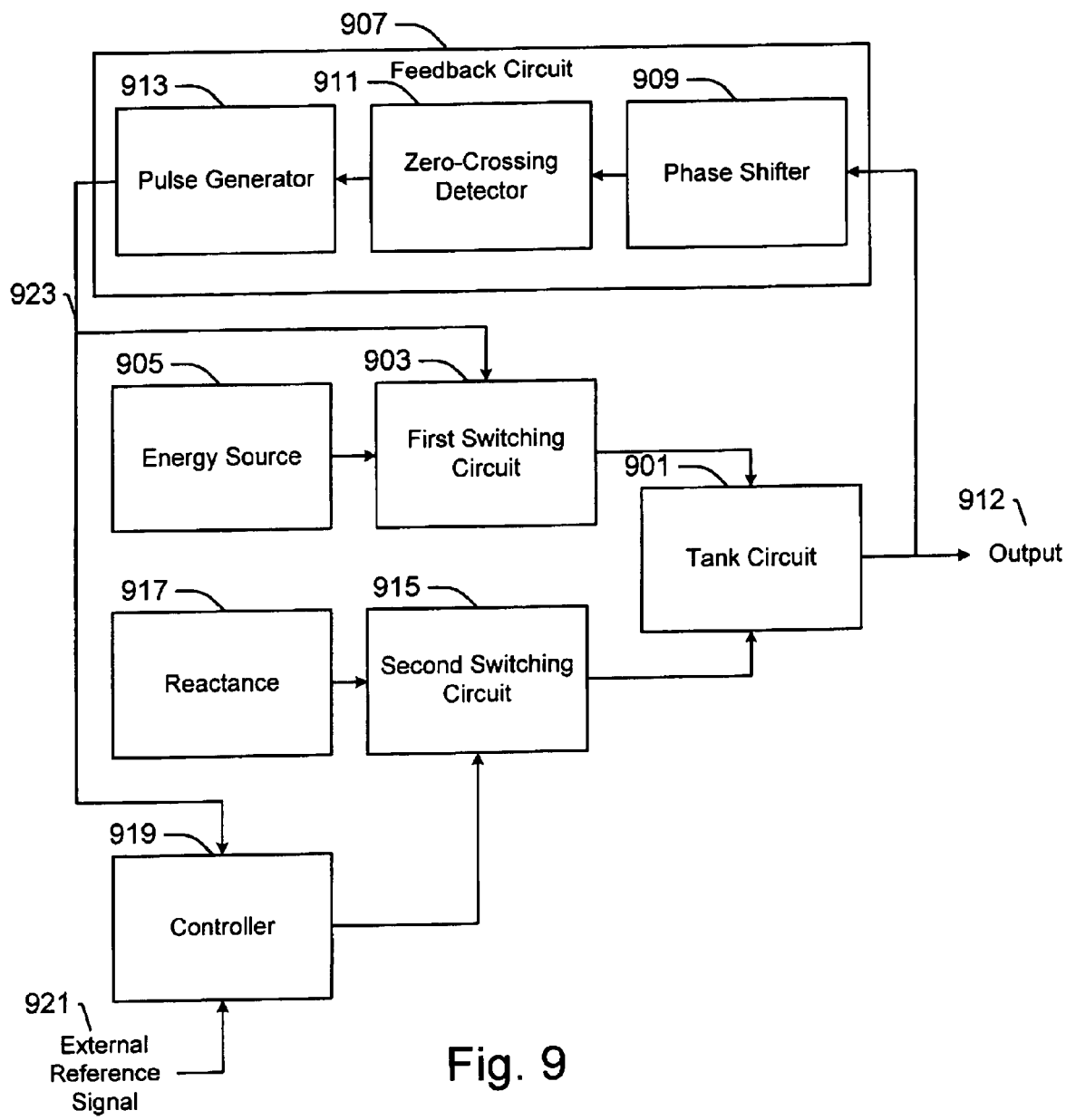
FIG. 9 is a block diagram of an E-Class oscillator configured to lock to an external reference signal.

FIG. 9 is a block diagram of an E-Class oscillator configured to lock to an external reference signal. As shown in FIG. 9, a tank circuit 901 may be configured to oscillate. To maintain these oscillations, a first switching circuit 903 may be configured to repeatedly add energy to the tank circuit 901 from an energy source 905. A feedback circuit 907 may be used to develop a drive signal 923 that controls the switching of the first switching circuit 903. The feedback circuit 907 may include a phase shifter 909 that may shift the phase of the output 912 from the tank circuit 901, such as, for example, by about 90 degrees, a zero-crossing detector 911 that may detect zero crossings of the phase-shifted signal from the phase shifter 909, and a pulse generator 913 that may generate a pulse each time a zero crossing is detected by the zero-crossing detector 911.

A second switching circuit 915 may controllably switch a reactance 917 in and out of the tank circuit 901, thus causing a change in the oscillation frequency generated by the tank circuit 901 each time the switch is made. The control signal to the second switching circuit 915, which determines when the second switching circuit 915 switches the reactance 917 in and out of the tank circuit 901, may be generated by a controller 919. The controller may generate the control signal that is delivered to the second switching circuit 915 based on an external reference signal 921 and the drive signal 923.

More specifically, the controller 919 may direct second switching circuit 915 to add the reactance 917 to the tank circuit 901 in response to the external reference signal 921 or to the drive signal 923. The controller 919 may also direct the second switching circuit 915 to remove the reactance 917 from the tank circuit 901 in response to the other of these two signals. In other words, the external reference signal 921 may be used in one embodiment to either add or remove the reactance 917 from the tank circuit 901; while the drive signal 923 may be used to cause the opposite operation.

Figure 10:
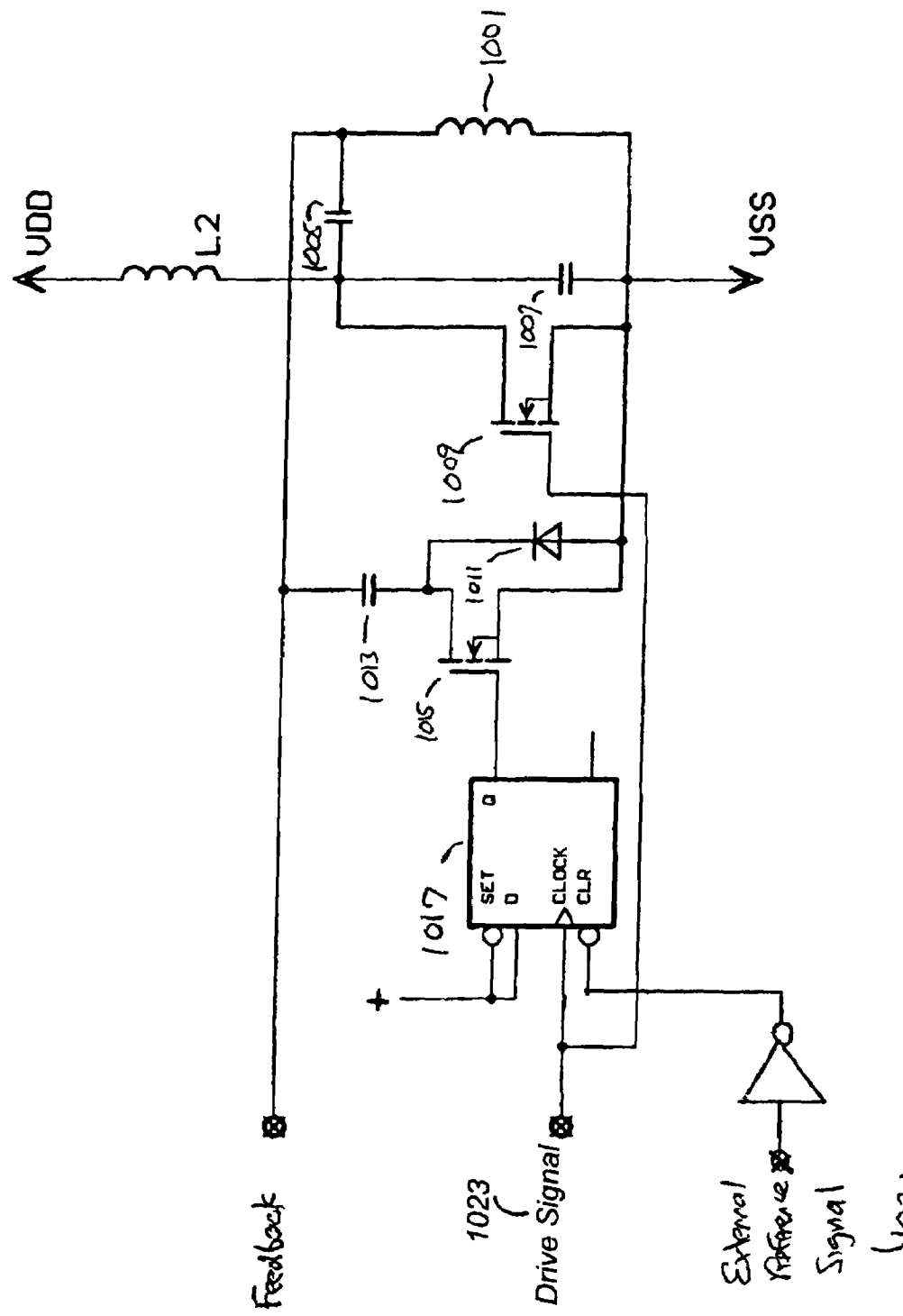
FIG. 10 is a schematic diagram of a portion of one embodiment of the E-Class oscillator illustrated in FIG. 9.

FIG. 10 is a schematic diagram of a portion of one embodiment of the E-Class oscillator illustrated in FIG. 9. Much of FIG. 10 corresponds to the similarly located components in FIG. 8 and described above, including coil 1001, capacitor 1005, capacitor 1007, switch 1009, diode 1011, capacitor 1013 and switch 1015.

Many of the components shown in FIG. 10 also are illustrative embodiments of some of the components shown in FIG. 9. For example, inductor 1001 and capacitor 1005 are an example of the tank circuit 901; the switch 1009 is an example of the first switching circuit 903; the capacitor 1007 is an example of the energy source 905; the switch 1015 is an example of the second switching circuit 915; and the capacitor 1013 is an example of the reactance 917. Each of these components may function as described above in connection with FIG. 8.

An example of the feedback circuit 907 is similarly illustrated in FIGS. 6 and 8. An example of the phase shifter 909 is the phase offset circuit; an example of the zero crossing detector 911 is the zero cross detector circuit; and an example of the pulse generator 913 is the combination of the start oscillator and drive pulse generator. The discussion of these components above in connection with FIG. 6 and FIG. 8 apply equally here.

FIG. 10 may also have a D memory 1017 that is configured to serve as one embodiment of the controller 919 shown in FIG. 9.

An external reference signal 1021 may have a rising edge. This rising edge, in turn, may clear the D memory 1017, opening the switch 1015 and removing the capacitor 1013 from the tank circuit. This may cause the tank circuit to oscillate at its maximum frequency.

A rising edge of the drive signal 1023, in turn, may clock the D memory 1017, thus closing the switch 1015 and placing the capacitor 1013 in the tank circuit. This may decrease the oscillation frequency of the tank circuit. As explained above in connection with FIG. 9, however, the drive signal 1023 may be derived from a feedback circuit 907, such as the feedback circuits shown in FIGS. 6 and 8. In this embodiment, the decrease in the frequency of the oscillation that is caused by activation of the drive signal may, in turn, reduce the frequency of the drive signal. This, in turn, increases the period during which each cycle of the internal reference signal 1021 causes an increase in the frequency of the oscillation. This feedback may ultimately cause the frequency of the oscillation in the tank circuit to synchronize and thus lock to the frequency of the external reference signal 1021.

Once the frequency of the E-Class oscillator illustrated in part in FIG. 10 is locked to the frequency of the external reference signal 1021, the phase of the oscillation in the tank circuit shown in FIG. 10 may be modulated by modulating the phase of the external reference signal 1021. After each shift in the phase of the external reference signal 1021, the circuit illustrated in part in FIG. 10 will cause a corresponding shift in the phase of the oscillation produced in the tank circuit. A few cycles may be needed before the lock is substantially complete.

Although FIG. 9 illustrates the switching in and out of a reactance 917 as the technique of controllably altering the frequency of the tank circuit 901, it is to be understood that other techniques could be used instead or in addition. For example, a varactor diode could be used instead of the capacitor 1013 with the output of the switch 1015 being used to control the input to the varactor diode. Other frequency-shifting techniques may also be used.

The foregoing description of the preferred embodiments of the invention has been presented for the purposes of illustration and description. It is not intended to be exhaustive or to limit the invention to the precise form disclosed. Many modifications and variations are possible in light of the above teaching. For example, a variety of alternative components may be utilized in the novel oscillator design of the present invention, as will be recognized by those skilled in the art, to build an oscillator that functions according to the teachings herein. It is intended that the scope of the invention be limited not by this detailed description, but rather by the claims appended hereto.

I claim:

1. An E-Class oscillator configured to lock to an external reference signal comprising:
   a tank circuit configured to oscillate;
   a first switching circuit configured to repeatedly add energy into the tank circuit in response to a drive signal to maintain the oscillation of the tank circuit;
   a second switching circuit configured to controllably alter the oscillation frequency of the tank circuit; and a controller configured to generate a control signal based on the external reference signal and based on the drive signal that causes the second switching circuit to repeatedly alter the oscillation frequency of the tank circuit in a manner that causes the oscillator to lock to the external reference signal.

2. The E-Class oscillator of claim 1 wherein the controller includes a D memory.

3. The E-Class oscillator of claim 2 wherein the D memory has a clear input and wherein the clear input is configured to be in communication with the external reference signal.

4. The E-Class oscillator of claim 2 wherein the D memory has a clock input and wherein the clock input is configured to be in communication with the drive signal.

5. The E-Class oscillator of claim 4 wherein the D memory has a clear input and wherein the clear input is configured to be in communication with the external reference signal.

6. The E-Class oscillator of claim 1 further including a feedback circuit in communication with the tank circuit that is configured to generate the drive signal.

7. The E-Class oscillator of claim 6 wherein the feedback circuit includes a zero crossing detector and a pulse generator circuit.

8. The E-Class oscillator of claim 7 wherein the feedback circuit includes a phase shifter circuit.

9. The E-Class oscillator of claim 1 wherein the controller is configured to repeatedly alter the oscillation frequency by repeatedly increasing the frequency in response to either the external reference signal or to the drive signal and by repeatedly decreasing the frequency in response to the other of these signals.

10. The E-Class oscillator of claim 9 further including a reactance that is configured to be added to and removed from the tank circuit by the second switching circuit.

11. The E-Class oscillator of claim 10 wherein the controller is configured to repeatedly add the reactance to the tank circuit in response to either the external reference signal or to the drive signal and to repeatedly remove the reactance from the tank circuit in response to the other of these signals.

12. A process for locking an E class oscillator having a tank circuit to an external reference signal comprising:
  repeatedly adding energy into the tank circuit in response to a drive signal; and
  repeatedly altering the oscillation frequency of the tank circuit in response to the drive signal and the external reference signal in a manner that causes the oscillator to lock to the external reference signal.

13. The process of claim 12 wherein the oscillator also includes a reactance and wherein the repeatedly altering the oscillation frequency includes:
  repeatedly adding the reactance to the tank circuit in response to either the external reference signal or to the drive signal; and
  repeatedly removing the reactance from the tank circuit in response to the other of these signals.

14. The process of claim 12 wherein the frequency of the external reference signal is modulated and wherein the frequency of the E-Class oscillator tracks the modulation.

15. The process of claim 12 wherein the phase of the external reference signal is modulated and wherein the phase of the E-Class oscillator tracks the modulation.

16. A process for modulating the phase of an E-Class oscillator in accordance with the modulated phase of an external reference signal comprising repeatedly altering the frequency of the oscillator in response to the external reference signal in a manner that causes the phase of the oscillator to substantially track changes in the phase of the external reference signal.

17. The process of claim 16 wherein the E-Class oscillator includes a tank circuit and wherein the repeatedly altering the oscillation frequency includes repeatedly adding the reactance to and removing it from the tank circuit.

* * * * *